United States Patent [19]
Ricciardelli

[11] Patent Number: 4,997,463
[45] Date of Patent: Mar. 5, 1991

[54] GAS-LIQUID MICROVOLUME SEPARATING APPARATUS AND METHOD

[75] Inventor: Robert H. Ricciardelli, Waukesha, Wis.

[73] Assignee: Frederick William Ricciardelli, Peabody, Mass.

[21] Appl. No.: 523,306

[22] Filed: May 11, 1990

Related U.S. Application Data

[63] Continuation of Ser. No. 255,553, Oct. 7, 1988, abandoned.

[51] Int. Cl.$^5$ ............................................. B01D 53/24
[52] U.S. Cl. ........................................ 55/165; 55/189; 55/204; 128/718; 128/719; 128/730
[58] Field of Search ................ 55/185, 189, 192, 204, 55/257, 165; 128/716, 718, 719, 730

[56] References Cited

U.S. PATENT DOCUMENTS

| | | | |
|---|---|---|---|
| 3,640,822 | 2/1972 | Hrdina | 55/55 X |
| 3,996,027 | 12/1976 | Schnell et al. | 55/52 X |
| 4,099,939 | 7/1978 | Vancheri et al. | 55/246 |
| 4,197,858 | 4/1980 | Osborn | 128/718 |
| 4,272,257 | 7/1981 | Ellion et al. | 55/38 |
| 4,274,425 | 6/1981 | Lutz et al. | 128/719 |
| 4,304,578 | 12/1981 | Hakala et al. | 55/189 |
| 4,382,806 | 5/1983 | Hakala et al. | 55/18 |
| 4,446,869 | 5/1984 | Knodle | 128/716 |
| 4,579,568 | 4/1986 | Ricciardelli et al. | 155/189 |
| 4,592,368 | 6/1986 | Ricciardelli et al. | 128/719 |
| 4,713,095 | 12/1987 | Ricciardelli | 55/189 |
| 4,717,403 | 1/1988 | Choksi | 55/429 |

Primary Examiner—Charles Hart
Attorney, Agent, or Firm—Townsend and Townsend

[57] ABSTRACT

A gas-liquid separator apparatus and device, particularly for use in connection with medical gas analyses, such as capnography, is provided. The separation chamber tapers in a direction from the blow down port to the dry gas outlet port providing increased surface area in the lower portion of the separation chamber for providing capillary volumes or regions. A solid body is disposed in the separation chamber to provide a surface of the capillary volumes and to decrease the effective volume of the separation chamber. The body can be used to occlude the dry gas outlet port upon tipping of the separation chamber at greater than a predetermined angle. A number of internal fins extend inwardly from the side wall and bottom surface into the separation chamber to form capillary volumes in cooperation with the side wall, bottom surface and/or solid body.

45 Claims, 4 Drawing Sheets

GAS-LIQUID MICROVOLUME SEPARATING APPARATUS AND METHOD

This is a continuation of application Ser. No. 07/255,553, filed Oct. 7, 1988, now abandoned.

FIELD OF THE INVENTION

The present invention relates to apparatus and method for separating liquid from a mixture of liquid and gas and, in particular, to a separating apparatus and method with a microvolume usable in connection with gas analyzers such as blood gas analyzers.

BACKGROUND OF THE INVENTION

In a number of medical procedures, it is desired to obtain an indication of the concentration of carbon dioxide in the exhaled breath of a patient. This determination, generally known as capnography, is typically conducted using an infrared analysis device. Such devices typically require that the gas being monitored be substantially dry, i.e., free from condensed water or other liquid constituents. Because exhaled gases typically exit a patient at about 100% relative humidity, as the gas cools during travel through the sampling line and equipment, moisture condenses. It is important to remove this moisture from the gas sample which is typically continuously drawn from the exhaled gases, usually at a flow rate of about 200 ml per minute or less.

Because, in capnography, it is desired to obtain continuous and instantaneous indications of the constitution of the exhaled gases, it is also important to avoid substantial mixing of gases sampled at different times. Accordingly, to avoid dampening the capnographic signal, the internal volume of the sampling line, including the volume of any gas/liquid separators, is preferably kept as small as possible. For this reason, it is generally desirable that a gas/liquid separating apparatus employ a separating chamber having a microvolume, i.e., a volume less than about 1 ml, and preferably much smaller.

Several approaches to solving these problems have been tried. U.S. Pat. No. 4,304,578 issued Dec. 8, 1981 to Hakala, et al. discloses a water separator which includes a downward tapering conical separation chamber. U.S. Pat. No. 4,382,806 issued May 10, 1983 to Hakala, et al. discloses a separation chamber with straight sides for precipitation of condensed water and a downward tapering portion at the lower end. U.S. Pat. Nos. 4,579,568 issued Apr. 1, 1986 to Ricciardelli, et al. and 4,592,368 issued June 3, 1986 to Ricciardelli, et al. disclose a separation chamber with a barrier which prevents direct flow to a second chamber that diverges upwardly. U.S. Pat. No. 4,717,403 issued Jan. 5, 1988 to Choksi discloses an apparatus which uses centrifugal separation of the gas and condensed moisture.

Of the above-described approaches, none describes making use of capillary forces or methods for No. 4,703,095 issued Dec. 15, 1987 to Ricciardelli discloses a separator with downwardly tapering pyramid-shaped lower walls forming internal corners with angles that produce capillary action for use in separation of a liquid from a gas. The capillary internal corners converge towards the liquid port to channel liquid away from the gas outlet port. Because of the downward tapering configuration of the separation chamber, a smaller interior wall surface area is available for formation of capillary volumes toward the bottom of the separation chamber. The total capillary volume in the lower area of the separation chamber thus is less than that in the upper region of the separation chamber. Accordingly, it would be useful to provide a separation configuration in which more surface area is available for capillary action in the lower portions of the separation chamber, without sacrificing effectiveness or efficiency of the capillary action.

Previously available separators of this type also have been subject to other disadvantages. Typical separators withdraw some amount of gas along with the separated liquid which is, therefore, not transmitted to the gas analysis device. This so-called blow down gas is preferably minimized because blow down gas is not available to the gas analyzer. Although previous devices are disclosed as requiring as little as 2 to 5% blow down for water separation, in practice it has been found that separation of liquids with viscosity higher than water (such as typically occurs when bodily fluids are mixed in the exhaled gases) require an increase in blow down ratio, occasionally greater than 15 to 20%. Accordingly, it would be useful to provide an apparatus with sufficient separation efficiency that the blow down ratio can be maintained less than about 15% even when the viscosity of the liquid is greater than that of water.

As noted above, it is desirable, in order to avoid damping or otherwise distorting the capnographic signal, that the separation chamber be kept at a small volume. Accordingly, it is desirable to provide a separation chamber with means for reducing the volume occupied by gas by substantial amounts such as 0.04 ml or more, to provide a dead space having a volume of about 0.1 ml or less.

Previous devices typically rely exclusively on gravitational means for separation or for channelling separated liquid away from the dry gas outlet port. Accordingly, previous devices are unusable when tilted substantially out of the preferred operating orientation or in reduced or zero gravity conditions. Accordingly, it would be useful to provide a device which will operate when tilted in positions up to 90° from the vertical or in a reduced or zero gravity environment.

Relatedly, previous devices, if tipped out of the preferred orientation, will permit liquid to exit from the dry gas outlet port causing fouling of the gas analyzer and consequent expensive cleaning or repairs. Accordingly, it would be useful to provide an apparatus in which tilting at greater than a predetermined angle results in prevention of the passage of liquid through the dry gas outlet port.

Because of the time and expense involved in sterilizing medical equipment, it would be also be advantageous to provide a device in which the regions which might become contaminated with the separated liquid are detachable from the remainder of the apparatus and are constructed using sufficiently inexpensive procedures and materials that such portions can be disposed of rather than cleaned and reused.

SUMMARY OF THE INVENTION

The separation chamber provided in the present invention is defined by interior surfaces which taper upwardly so that the cross-sectional area in the lower portion of the separation chamber exceeds the cross-sectional area of the upper portion.

Accordingly, the interior surface area of the separation chamber is greater in the lower portion, affording larger surface areas for provision of capillary channels or volumes. The more effective capillary action provided by the present invention contributes to more efficient separation, even for higher viscosity fluids, and thus a lower blow down ratio requirement. Furthermore, the higher efficiency of capillary action permits utilization of the separation chamber even when tilted from the vertical such as up to 90° or in reduced or zero gravity environments. A solid movable body such as a ball bearing is disposed in the separation chamber. The ball bearing in the lower position acts to form a surface of the capillary volumes, further increasing capillary action efficiency. The movable body also occupies space and thereby reduces the effective volume of the separation chamber. When the separation chamber is tipped at greater than a predetermined angle, the ball bearing occludes the outlet port preventing passage of liquid and consequent fouling of the analyzer. Preferably, a device such as a magnet is used to position and maintain the ball bearing in the occluded position upon tipping beyond a predetermined angle.

An outlet port from the separation chamber conveys the separated liquid and the blow down gas to a reservoir. The reservoir may include an absorbing material to assist in preventing moisture from being drawn into the blow down port when the device is tilted. Additionally, the absorbing material can be selected to have large expansion when wetted to provide an indication when the reservoir is filled.

DETAILED DESCRIPTION OF THE PREFERRED EMBODIMENTS

Figure 1:
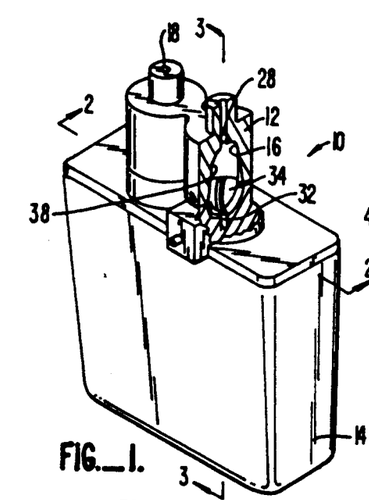
FIG. 1 is a perspective view of a disposable separation apparatus according to the present invention.
Figure 2:
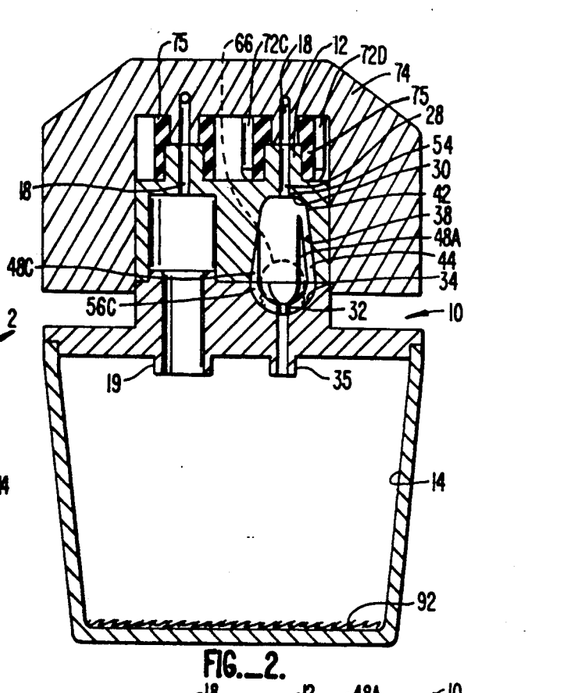
FIG. 2 is a frontal cross section taken along line 2—2 of FIG. 2, additionally showing a housing in cross section.
Figure 3:
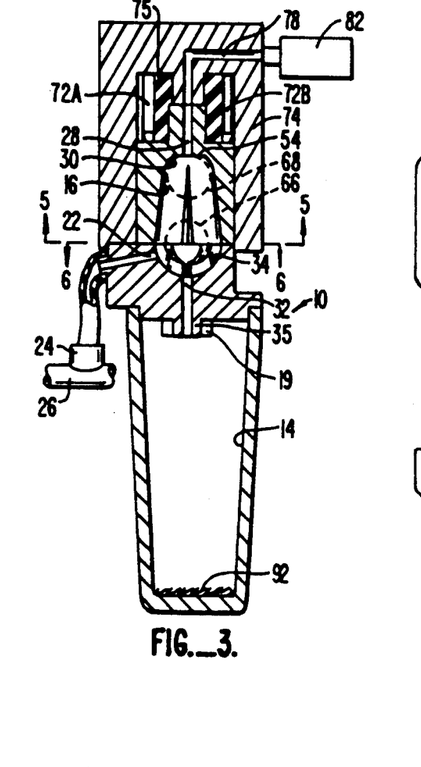
FIG. 3 is a cross section of the embodiment of FIG. 2 taken along line 3—3 of FIG. 1, additionally showing a housing in cross section.
Figure 4:
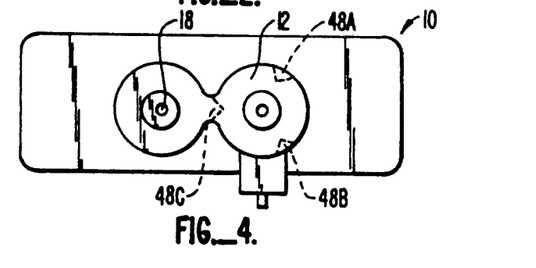
FIG. 4 is a top view of the apparatus of FIG. 1.
Figure 5:
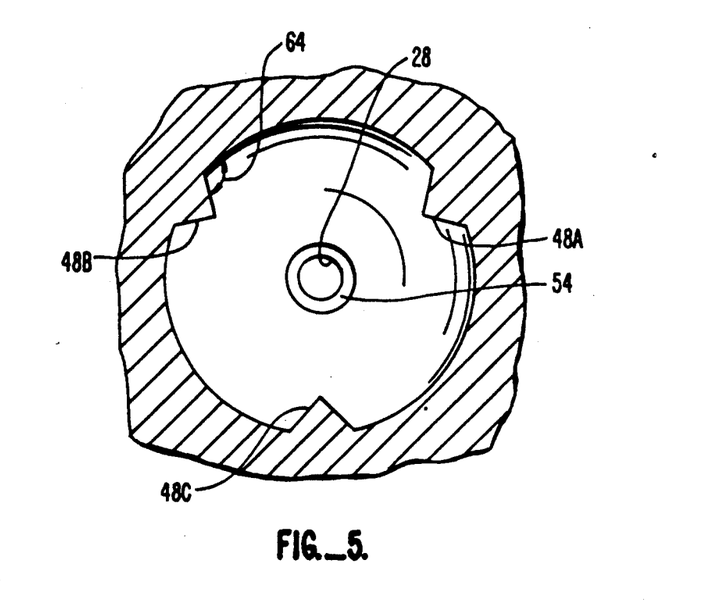
FIG. 5 is a partial cross section taken along line 5—5 of FIG. 3.
Figure 8:
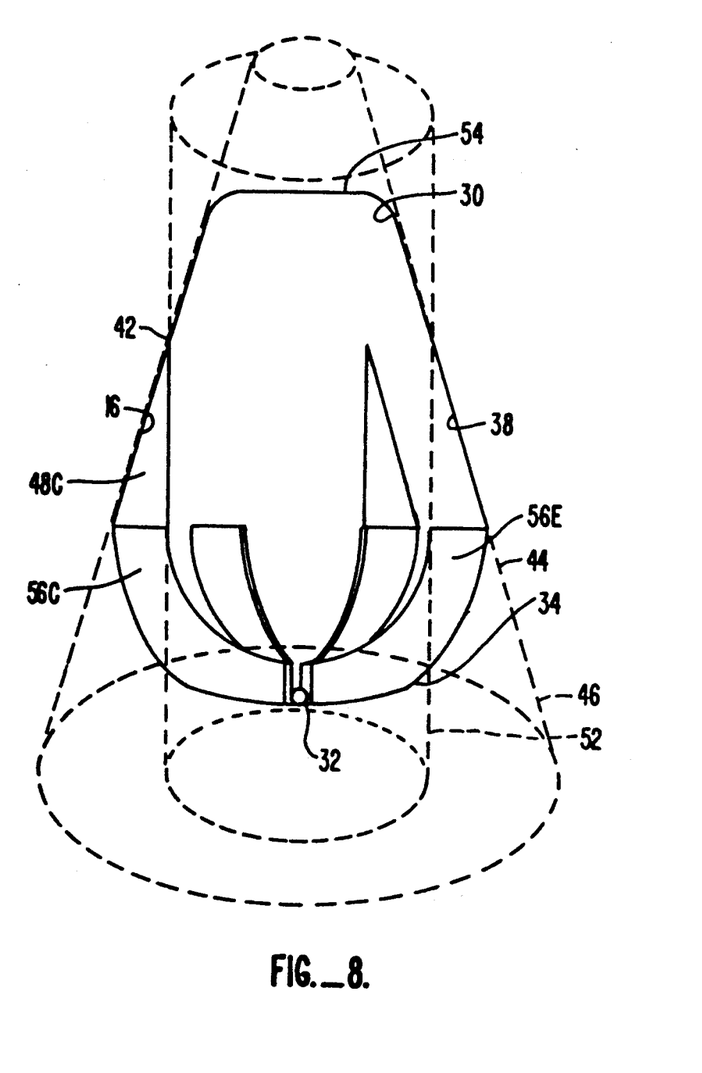
FIG. 8 is a schematic depiction of the separation chamber showing conical and cylindrical surfaces.
Figure 9:
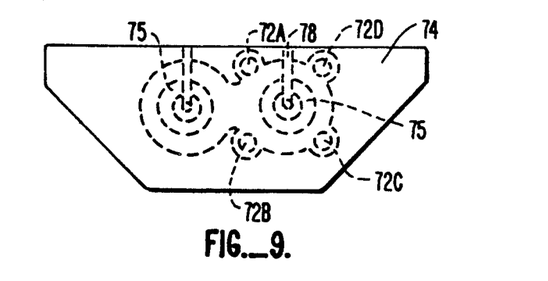
FIG. 9 is a top plan view of the housing.

Referring to FIG. 1, a separator 10 according to the present invention includes a manifold portion 12 in fluid communication with a reservoir 14. As best seen in FIG. 2, the manifold 12 contains a separation chamber 16 and a low-pressure passageway 18. The low-pressure passageway 18 communicates with the reservoir 14 by a first tube 19. The separation chamber 16 has three ports. An inlet port 22, best seen in FIG. 3, is used for transmitting a sample of the patient s exhalation gases obtained by means of a sampling device 24 of any of the types well known in the art, connected to the exhalation gas passageway 26 from the patient. A first outlet port 28 is provided in the first, normally upper end surface 30 of the separation chamber 16 for removal of substantially dry gas. A second outlet port 32 is provided in the second, normally lower end surface 34 of the separation chamber for conveyance of a mixture of substantially all liquid and a blow down portion of gas into the reservoir 14 by way of a second tube 35 extending partially into the reservoir 14. The first end surface 30 and the second end surface 34 are connected by a sidewall 38. The sidewall 38 defines the cross-sectional area at any point along the longitudinal extent of the separation chamber 16, which varies in such a way that the cross-sectional area in the region adjacent to the first end surface 42 is less than the cross-sectional area in the region adjacent to the second end surface 44. Preferably, the sidewall 38 defines a substantially conical surface, i.e., lies substantially along an imaginary cone 46, as best seen in FIG. 8. Extending inward from the sidewall 38 into the interior of the separation chamber 16 are one or more upper fins 48. Preferably, the apices, or inward-most extent of the upper fins 48, define a cylinder, i.e., lie substantially along an imaginary cylindrical surface 52. In the embodiment depicted in FIGS. 1–8, there are three fins 48a, 48b, and 48c, of substantially triangular cross-sectional shape.

The upper fins 48 act to position and guide movement of an interior body, as described more fully below, and can also form a surface of a capillary region or volume in cooperation with the sidewall 38, as described more fully below. Because whether a region or volume will have a capillary action on a fluid depends on the characteristics of the fluid, principally the surface tension thereof, the geometry and dimensions of a capillary volume must be defined in relationship to the fluid. In the present case, a contemplated use of the invention is separation of liquid from exhaled gases. In many instances, the liquid will be substantially water, and thus the present invention includes volumes which are capillary volumes with respect to water. As noted above, however, in many medical applications, the liquid will include an amount of typically viscous body fluids, so that preferably the capillary volumes will be capillary with respect to fluids which are more viscous than water.

Preferably, the upper fins 48 extend only partly along the longitudinal extent of the sidewall 38 and are sufficiently spaced from the first outlet port 28 to prevent any capillary conveyance of liquid to the vicinity of the outlet port 28, such as might result in movement of liquid through the first outlet port 28.

The first end surface 30 is substantially shaped as a segment of a sphere, such as a hemisphere, with a planar portion 54 to assist in occlusion of the first outlet port 28, as described more fully below. The first outlet port 28 is preferably centrally located in the planar portion 54.

Figure 6:
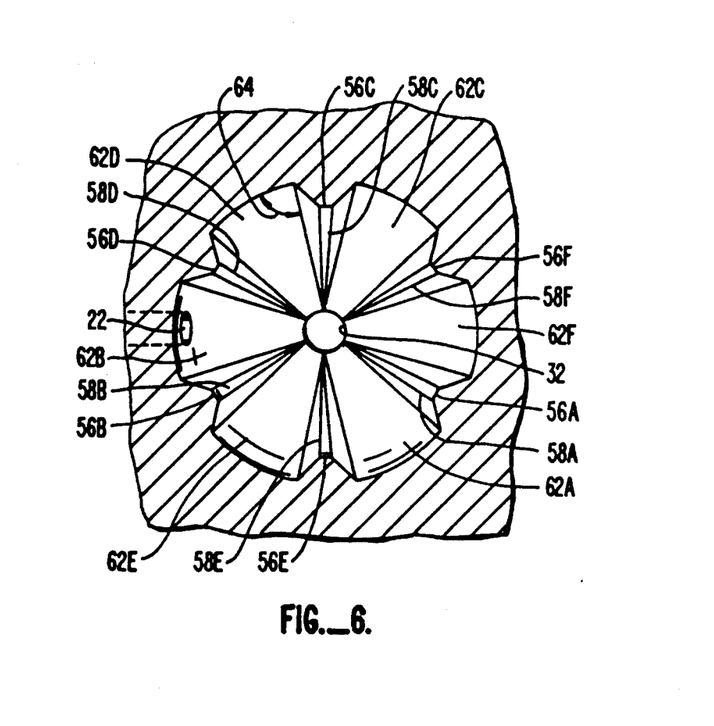
FIG. 6 is a partial cross section taken along line 6—6 of FIG. 3.
Figure 7:
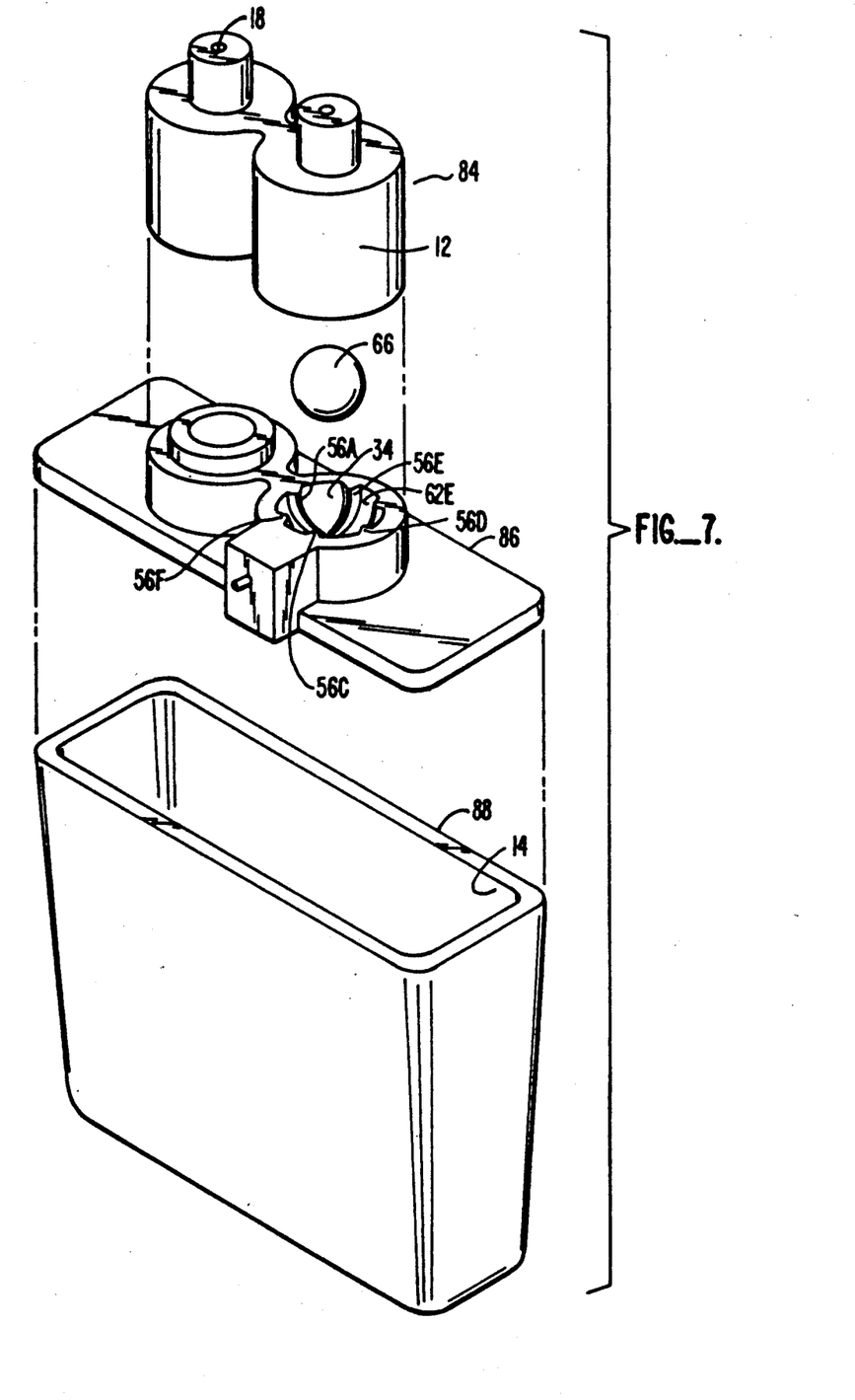
FIG. 7 is an exploded perspective view of apparatus of FIG. 1 showing a preferred method of assembly.

The second outlet port 32 is adjacent to, and preferably formed in, the second end surface 34. The second end surface 34 is preferably shaped as a segment of a sphere, such as a hemisphere. A plurality of lower fins 56 project inward from the second end surface 34 into the interior of the separation chamber 16, as best seen in FIG. 7. The lower fins 56 act to position a solid body in the separation chamber 16 and to define capillary regions or volumes, as described more fully below. As best seen in FIG. 6, the lower fins 56 are substantially trapezoidal in cross section so that the innermost extensions or surfaces 58 of the lower fins 56 are substantially flat.

In the embodiment depicted in FIGS. 1–8, six lower fins, 56a–56f, are provided, preferably radially disposed about the second outlet port 32. Preferably, the flat surfaces 58 define a spherical surface, i.e., lie along a sector of an imaginary sphere, substantially parallel to the second end surface 34.

The fins 56, in cooperation with the second end surface 34, form walls of capillary regions or volumes. The capillary volumes include the interstices 62a–62f between the lower fins 56. It has been found that a converging configuration of capillary volumes 62, such as that depicted in FIGS. 1–8, is effective to convey liquid towards the second outlet port 32 with sufficient efficiency that even when the liquid has a viscosity higher than water, the amount of gas flow or blow down needed to convey the liquid away from the first outlet port 28 and into the reservoir 14 is less than in previous configurations. Without wishing to be bound by any theory, it is believed that the efficiency is related to providing both capillary volumes 62, which taper towards the second outlet port 32, and a relatively large surface area in the second end surface 31 for accommodating more capillary volumes 62. The tapering of the sidewall 38 is consistent with both the desirably of a large surface area for the second end surface 34, and the desirability of a small total volume for the separation chamber 16.

Another advantage of increased capillary effect of the present configuration is that the device is less dependent on gravitational action than previous devices. Accordingly, the present invention is operable when tipped, such as at angles up to about 90°, so that gravity is not acting in a direction toward the second outlet port, and is also operable in low or zero gravity environments.

As noted, for example, in U.S. Pat. No. 4,713,095, the angle of corners affects the degree of capillary action of a capillary volume. Accordingly, in the preferred embodiment, the angle 64 which the lower fins 56 make with the second end surface 34 is preferably less than or equal to about 135°. This angular relationship is preferably also used in the upper fins 48.

Although the lower fins 56, acting only in cooperation with the second end surface 34, can be configured to provide capillary volumes 62 with the desired efficiency, in the preferred embodiment a solid body, such as a ball bearing 66 is disposed in the separation chamber 16 to also define surfaces of capillary volumes. The ball bearing 66 is positionable to substantially contact the flat surfaces 58 of the lower fins 56 and, in this position, to form an additional surface to define the capillary volumes 62. Thus, in the preferred embodiment, the capillary volumes 62a–62f are defined by the fins 56a–56f, the second end surface 34, and portions of the surface of the ball bearing 66. The presence of the ball bearing has been found to increase the efficiency of the capillary action, and thus permit a lowering of the blow down ratio (i.e., the percentage or portion of the gas which is introduced into the separation chamber that is drawn through the second outlet port 32), which is necessary to remove liquid from the separation chamber 16 so as to prevent its passage through the first outlet port 28. In one embodiment of the invention, the solid body is fixed, such as by gluing, in a position away from the first outlet port 28 and proximate to, but spaced from, the second outlet port, such as the position 66 depicted in FIG. 3, to be in a non-sealing relationship with the second outlet port 32.

The ball bearing 66 is also operable to provide other functions. Because the ball bearing occupies a certain amount of space in the separation chamber 16, the effective volume (i.e., the dead space or volume available for the gas) is reduced, thus reducing or preventing degradation of the gas analysis signal because of excessive gas mixing in the separation chamber 16.

Further, the ball bearing 16 can act to occlude the first outlet port 28 when such is desired. For example, it may be desired to occlude the first outlet port 28 whenever the separation chamber 16 is tipped out of its preferred vertical alignment, depicted in FIG. 3, beyond a predetermined maximum tipping angle, such as tipping to such a degree that liquid in the separation chamber 16 or reservoir 14 will flow through the first outlet port 28. Preferably, the upper fins 48 are configured to guide the ball bearing 66 from the lower position depicted in FIG. 3 to an upper position 68, shown in phantom lines. It is for this reason that the upper fins 48 define a substantially cylindrical surface 52 for passage of the substantially spherical ball bearing 66. It has been found that the desired seating of the ball bearing 66 to occlude the first outlet port 28 is facilitated by provision of the planar region 54 around the first outlet port 28.

The maximum tipping angle, beyond which it is desired to occlude the first outlet port 28, will depend on the configuration of the separation chamber 16 and the outlet ports 28, 32. In part because of the upward tapering configuration of the sidewall 38, a larger tipping angle can be tolerated in the present invention than could be tolerated by previous downward tapering configurations. In general terms, the maximum tipping angle will be that angle at which either a portion of the sidewall 38 is angled sufficiently downward with respect to gravity to permit liquid to flow into the first outlet port 28, or at which liquid in the reservoir 14 can freely flow into the separation chamber 16 under the influence of gravity. Accordingly, the maximum tipping angle is affected by the geometry of the separation chamber 16 and reservoir 14. The downward tapering of the separation chamber permits toleration of a larger tipping angle than could be permitted with an untapered or oppositely tapered chamber. Further, the extension of the first and second tubes, 19, 35 into the reservoir 14 permits some degree of tipping (and thus, pooling of liquid near the top of the reservoir 14) before liquid can pass back into the separation chamber 16.

The angle at which the ball bearing 66 moves to the second or upper position 68 can be adjusted or affected by the configuration of the sidewall 38 or upper fins 48 so that movement is controlled only by gravitational forces. Preferably, however, a device is provided to position and maintain the ball bearing 66 in the upper position 68 upon tipping beyond a predetermined angle. In the embodiment depicted in FIG. 3, the device for positioning and maintaining the ball bearing 66 in the upper position 68 is an array of four magnets 72A–D. A number of advantages are obtained by using a positioning device such as a magnet 72. The strength of the magnets 72A–D can be adjusted so that they are effective to position the ball bearing 66 in the upper position 68 as soon as the ball bearing 66 has moved to within a predetermined distance of the magnets 72A–D, such as from tipping of the separation chamber 16. In this manner, it is possible to adjust the tipping angle at which the ball bearing 66 is moved to the upper, occluding position 68. By using an electromagnet, rather than a permanent magnet, the strength of the magnetic field can be calibrated to adjust the maximum permissible tipping angle, or the electromagnet can be activated by an angle-sensing device (not shown). Further, because the relatively more expensive magnet 72 is a part of the housing 74, rather than part of the separator 10, the overall cost of the separator 10 is maintainable at a level which permits the separator 10 to be used in a disposable fashion. Preferably, the magnets 72A-D are positioned slightly above the center of the ball bearing 66 when the ball bearing is in the upper position 68.

The housing 74 preferably contains apparatus, such as resilient sleeve 75, for holding the separator 10 in position so as to permit easy detachability and replacement of the separator 10 consistent with its preferred use as a disposable member. The housing 74 also contains a passageway 78 for conveying gas from the first outlet port 28 to the gas analyzer 82, which can be any gas analyzer, such as an infrared capnogram or others well known in the art.

FIG. 7 depicts a preferred manner of assembly of the device. As shown, the device is preferably formed from three sections, an upper manifold section 84, a lower manifold section 86, and a reservoir section 88. Although the preferred material of construction is a clear polycarbonate material, other materials, such as metal, resins, plastics, and the like, can be used. The parts are preferably formed by molding, such as injection molding, but can be formed by other processes, such as stamping, milling, and the like. The parts 84, 86, 88 are preferably joined by a bonding technique, such as ultrasonic welding, although they can also be joined by adhesion, screwing, bolting, and other well known methods.

The exact dimensions and shapes of the apparatus will depend on the intended use. In one preferred embodiment, the interior volume of the separation chamber 16 is approximately 0.1 ml. The ball is 0.172 inches (about 4.4 mm) in diameter, and the imaginary cylinder defined by the upper fins has a diameter of about 0.18 inches (about 4.6 mm). The lower fins 56 define a spherical sector with a 0.184 inch diameter, whose center is 0.006 inches (about 0.15 mm) above the plane of the parting line. The second end surface 34 lies along a sphere of 0.224 inches in diameter (about 5.7 mm) whose center is coincident with the center of the sphere defined by the lower fins 56. The inlet port 22, first outlet port 28, and second outlet port 32 have diameters of approximately 0.03 inches (about 0.75 mm). The reservoir 14 has a capacity of about 0.3 cubic inches (about 5 ml). The upper end surface 30 lies partially along a spherical sector with a radius of 0.09 inches (about 2.3 mm).

The manner of operation of the present invention will now be described. Operation of a gas analysis system of a type usable in connection with the present invention is described in U.S. Pat. No. 4,592,368, albeit with another type of gas/liquid separator. In general, gas, such as exhaled gas from a patient, is conveyed through a passageway 26 and is sampled by a sampling device 24. A slight negative pressure is provided in the separation chamber 16 by virtue of negative pressures established at the low-pressure passageway 18 and the first outlet port 28, in a manner well known in capnography gas-liquid separators. Because of the lower pressure in the separation chamber 16, gas from the sampling device 24 enters the separation chamber 16 through the inlet port 22. The fluid entering inlet port 22 is a mixture of gas and liquid, the liquid typically being liquid which has condensed from the gas as it has cooled. The liquid impacts the interior surfaces of the separation chamber 16 and the ball bearing 66, and accumulates or coalesces in the capillary volumes 62. The coalescence in the capillary volumes 62 can be accomplished or enhanced by ordinary gravity drainage of droplets down the sidewall 38 and/or capillary conveyance along capillary volumes formed between the upper fins 48 and the sidewall 38. The liquid is directed, by capillary action and/or gravitational action, away from the first outlet port 28 and towards the second outlet port 32. Because of the relatively lower pressure in the reservoir 14, by virtue of the partial vacuum created through the low pressure passageway 18, substantially all liquid and the blow down portion of the gas are conveyed through the second outlet port 32 to the reservoir 14. The reservoir 14 is preferably provided with an absorbent material 92 to assist in preventing flow of liquid from the reservoir 14 into the separation chamber 16, such as upon tipping of the reservoir 14. Preferably, the absorbent material 92 expands upon wetting, and can be used to provide a visual indication of the amount of liquid in the reservoir 14, such as by providing a view port or window in the reservoir 14 or by forming reservoir 14 of a substantially transparent material.

Use of the separator 10 is continued until the reservoir 14 is substantially filled with liquid, for example, as indicated by expansion of material 92 in the reservoir 14. At this point, the separator 10 can be removed from the housing 74 and replaced by a new separator 10. Because substantially all patient-wetted surfaces are contained in the separator 10 or are upstream thereof, replacement of a separator 10 with a sterile separator prevents contamination of a new patient. Preferably, a removed separator 10 is disposed of, whereas the housing 74 is reusable.

When the separation chamber 16 is tipped beyond a predetermined angle, as described above, the ball bearing 66 is brought within the influence of a magnet 72, and the magnet positions the ball bearing 66 adjacent to and seating with respect to the first outlet port 28 to prevent the passage of liquid through the first outlet port 28.

As can be seen from the above description, a number of advantages are provided by the present invention. Capillary action in the present configuration is sufficiently effective to permit reduction of the blow down ratio, such as reduction below 15% even when fluids more viscous than water are separated. Upward tapering sidewalls provide for increased surfaces for capillary volumes in lower portions and increase in the permissible tipping angle without excessive increase in the volume of the separation chamber 16. A solid body, such as a ball bearing, provides for an additional surface for definition of capillary volumes, provides for a decrease in the effective volume of the separation chamber, and is usable for selective occlusion of the first outlet port, for example, upon tipping beyond a predetermined angle. The apparatus is inexpensively made, consistent with disposable use. The separator 10 is detachable in such a way that patient-wetted surfaces are removable from the housing to assist in preventing contamination from one patient to another.

Increased efficiency of capillary action contributes to greater liquid separation ability, and thus lowers the chance of passage of liquid through the first outlet port. Because movement of liquid to the second outlet port is effected, at least in part, by capillary action, the separator 10 is capable of operation in positions of up to 90° from the vertical, or in reduced or zero gravity conditions. The device will automatically shut off flow to the second outlet port if predetermined conditions of acceptable orientation are exceeded, thus preventing liquid from fouling the measuring device.

A number of variations and modifications of the invention can be practiced, including those described below. The sidewall of the separation chamber can be formed in a tapering configuration other than a conical configuration. The solid body, which is movable in the separation chamber, can be a body other than a ball bearing and other than a spherical body, although it is preferably gas-impermeable. The upper fins can define an imaginary surface other than a cylindrical surface, particularly in cooperation with a non-spherical movable body. Fins with non-triangular or non-trapezoidal cross sections are usable, although flat surfaces of contact with the movable body, particularly with respect to the lower fins, assist in preventing damage from impact between the movable body and the fins. The upper and lower end surfaces can have other than spherical sector configurations, consistent with channeling of flow to the outlet ports. Devices for positioning and maintaining the ball bearing in the upper position, other than a magnet, can be used, such as springs, electric devices, hydraulic or fluid devices, and the like. A gas analyzer, other than an infrared capnographic analyzer, can be used and the separator 10 can be used in non-gas analyzer contexts, such as any context in which it is desired to separate a liquid from a gas. Although the preferred use of the separator is as a disposable unit, the separator can be provided in a reusable and/or sterilizable configuration.

Although the invention has been described in terms of its preferred embodiment, modifications and variations are also included in the present invention, the scope of which is defined by the following claims.

What is claimed is:

1. In a system for analyzing samples of an exhaled mixture of gas and liquid, a fast-response apparatus usable for obtaining a substantially dry gas sample from a sample of said mixture of gas and liquid, comprising:
   a microvolume separation chamber defined by a first end surface, a second end surface, and a side wall, said side wall defining the cross-sectional area of said separation chamber, at least a portion of said sidewall being free from projections extending inward into said separation chamber;
   inlet port means for introducing a sample of said mixture of gas and liquid into said separation chamber in a radial direction towards the center of said separation chamber;
   first outlet port means for removing substantially dry gas for said analyzing, said outlet port means being substantially adjacent to said first end surface; and
   second outlet port means for removing a waste mixture of gas and liquid from said separation chamber for dispersal, said second outlet port means being substantially adjacent to said second end surface;
   at least one fin extending inward from said sidewall into said separation chamber wherein the cross-sectional area of said separation chamber adjacent to said first end surface is less than the cross-sectional area of said separation chamber adjacent to said second end surface.

2. An apparatus, as claimed in claim 1, wherein:
   the volume of said separation chamber which is occupied by said mixture of introduced gas and liquid is less than about 0.1 ml.

3. An apparatus, as claimed in claim 1, wherein:
   the viscosity of said liquid in said input mixture of gas and liquid is greater than the viscosity of water; and
   the rate of flow of said gas through said first outlet port is less than about 15% of the rate of flow of said gas through said inlet port means.

4. An apparatus, as claimed in claim 1, further comprising:
   reservoir means, spaced from said separation chamber in fluid communication with said second outlet port for holding the liquid in said waste mixture.

5. An apparatus, as claimed in claim 4, further comprising:
   liquid absorbing means disposed in said reservoir means.

6. An apparatus, as claimed in claim 4, further comprising:
   means for indicating the amount of liquid in said reservoir.

7. An apparatus, as claimed in claim 1, further comprising:
   means for substantially preventing flow of at least a portion of said separated liquid through said first outlet port means.

8. An apparatus, as claimed in claim 7, wherein said means for preventing flow comprises a substantially gas-impermeable body positioned in said separation chamber.

9. An apparatus, as claimed in claim 7, wherein said means for preventing flow comprises liquid-absorbing material positioned outside of said separation chamber and substantially proximate to said second outlet port means.

10. An apparatus, as claimed in claim 7, wherein said means for preventing flow comprises a tube extending in a direction away from said separation chamber in fluid communication with said second outlet port.

11. In a system for analyzing samples of an exhaled mixture of gas and liquid, a fast-response apparatus usable for obtaining a substantially dry gas sample from a sample of said mixture of gas and liquid, comprising:
   a microvolume separation chamber defined by a first end surface defining a first perimeter, a second end surface defining a second perimeter greater than said first perimeter, and a side wall, wherein said side wall substantially defines a portion of a cone tapering from said second end surface toward said first end surface and wherein at least a portion of said sidewall is free from projections extending inward into said separation chamber;
   inlet port means for introducing a sample of said mixture of gas and liquid into said separation chamber;
   first outlet port means for removing substantially dry gas for said analyzing, said first outlet port means being substantially adjacent to said first end surface;
   second outlet port means for removing a waste mixture of gas and liquid from said separation chamber for dispersal, said second outlet port means being substantially adjacent to said second end surface; and
   at least one fin extending inward from said side wall into said separation chamber.

12. An apparatus, as claimed in claim 11, wherein:
   said fin is configured to define, in cooperation with said side wall, a volume dimensioned to act as a capillary volume with respect to said liquid, said volume being in fluid communication with said second outlet port means and effective to convey said liquid toward said second outlet port means.

13. An apparatus, as claimed in claim 12, wherein:
said capillary volume is effective to convey said liquid toward said second outlet port means in a reduced gravity environment.

14. An apparatus, as claimed in claim 12, wherein:
said first outlet port is above said second outlet port when said separation chamber is in an upright position; and
said capillary volume is effective to convey said liquid toward said second outlet port means when said separation chamber is tipped from said upright position.

15. An apparatus, as claimed in claim 11, further comprising:
a plurality of fins extending inward from said side wall into said separation chamber, each fin having a region of inward-most extension, said regions of inward-most extension defining a substantially cylindrical surface.

16. An apparatus, as claimed in claim 11, further comprising:
means for automatically interrupting a flow through said first outlet port means when said separation chamber is tilted at greater than a predetermined angle.

17. An apparatus, as claimed in claim 16, wherein:
said means for interrupting flow comprises at least one substantially spherical body positioned in said separation chamber and movable with respect to said first outlet port means.

18. An apparatus, as claimed in claim 11, further comprising:
substantially gas-impermeable means for occupying volume in said separation chamber to reduce the effective separation chamber volume.

19. An apparatus, as claimed in claim 18, wherein said means for occupying volume comprises at least one substantially spherical body in said separation chamber, positioned to permit contact with said fin.

20. An apparatus, as claimed in claim 11, wherein:
said means for occupying volume has a volume of at least about 30% of the volume of said separation chamber.

21. In a system for analyzing samples of an exhaled mixture of gas and liquid, a fast-response apparatus usable for obtaining a substantially dry gas sample from a sample of said mixture of gas and liquid comprising:
a microvolume separation chamber having a surface;
inlet port means for introducing a sample of said mixture of gas and liquid into said separation chamber in a radial direction towards the center of said separation chamber;
first outlet port means for removing substantially dry gas for said analyzing;
second outlet port means for removal of a waste mixture of gas and liquid for disposal; and
a solid body, having a surface, positioned in said separation chamber to define an effective separation volume, said effective separation volume being the volume of said separation chamber minus the volume of said solid body;
said solid body being spaced from said surface of said separation chamber to produce at least a first capillary volume effective to convey at least some of said liquid toward said second outlet port means, said first capillary volume being at least partially defined by at least a portion of said surface of said solid body.

22. An apparatus, as claimed in claim 21, wherein:
said solid body is movable from a first position spaced from said first outlet port means to a second position substantially adjacent to and in sealing relationship to said first outlet port means.

23. An apparatus, as claimed in claim 21, further comprising:
means for maintaining said solid body in said second position when said separation chamber is tilted more than a predetermined angle.

24. An apparatus, as claimed in claim 23, wherein said means for maintaining comprises at least one magnet.

25. An apparatus, as claimed in claim 21, wherein:
said solid body comprises at least one ball bearing.

26. An apparatus, as claimed in claim 21, wherein:
said solid body comprises a material susceptible to magnetic attraction.

27. An apparatus, as claimed in claim 21, wherein:
said solid body is fixed in a position spaced from said first outlet port means and proximate to and in non-sealing relationship to said second outlet port means.

28. Apparatus, as claimed in claim 21, wherein said effective separation volume is less than about 0.1 milliliters.

29. Apparatus, as claimed in claim 21, wherein said surface of said separation chamber has at least a first portion free from inward projections and wherein at least one capillary volume is formed between said first portion of said surface of said separation chamber and a portion of the surface of said solid body.

30. Apparatus, as claimed in claim 21, wherein said surface of said separation chamber has at least a first inwardly projecting fin and wherein at least one capillary volume is formed between a portion of said fin and a portion of the surface of said solid body.

31. In a system for analyzing samples of an exhaled mixture of gas and liquid, a fast-response apparatus usable for obtaining a substantially dry gas mixture from a sample of said mixture of gas and liquid, comprising:
a microvolume separation chamber defined by a first end surface, a second end surface, and a side wall;
inlet port means for introducing a sample of said mixture of gas and liquid into said separation chamber;
first outlet port means for removing substantially dry gas for said analyzing, said first outlet port means being substantially adjacent to said first end surface;
second outlet port means for removing a waste mixture of gas and liquid from said separation chamber for disposal, said second outlet port means being substantially adjacent to said second end surface;
a substantially gas-impermeable body, having a surface, positioned in said separation chamber and movable with respect to said surfaces;
between a first position and a second position, said first position being closer to said second outlet port means than said second position, said gas-impermeable body, in said first position spaced from said second end surface to produce at least a first capillary volume effective to convey at least some of said liquid toward said second outlet port means, said first capillary volume being at least partially defined by at least a portion of said surface of said gas-impermeable body; and said microvolume separation chamber and said gas-impermeable body together defining an effective separation volume being the volume of said microvolume separation chamber minus the volume of said gas-impermeable body.

32. An apparatus, as claimed in claim 31, wherein:
said substantially gas-impermeable body comprises a substantially spherical body.

33. An apparatus, as claimed in claim 31, wherein:
said substantially gas-impermeable body comprises at least one ball bearing.

34. An apparatus, as claimed in claim 31, wherein:
when said separation chamber is tilted at an angle greater than a predetermined angle, said substantially gas-impermeable body occludes said first outlet port means wherein liquid is prevented from passing through said first outlet port means.

35. An apparatus, as claimed in claim 31, further comprising:
at least one fin projecting inward into said separation chamber from said second end surface; and
said substantially gas-impermeable body is positionable with respect to said fin to define, in cooperation with said second end surface, a volume dimensioned to act as a capillary volume with respect to said liquid, said volume being in fluid communication with said second outlet port means.

36. An apparatus, as claimed in claim 35, wherein:
said capillary volume tapers in cross-sectional area in a direction toward said second outlet port means.

37. Apparatus, as claimed in claim 31, wherein said effective separation volume is less than about 0.1 milliliters.

38. Apparatus, as claimed in claim 31, wherein said sidewall has at least a first portion free from inward projections and wherein at least one capillary volume is formed between said first portion of said sidewall and a portion of the surface of said gas-impermeable body.

39. Apparatus, as claimed in claim 31, wherein said sidewall has at least a first inwardly projecting fin and wherein at least one capillary volume is formed between a portion of said fin and a portion of the surface of said gas-impermeable body.

40. An apparatus usable for analyzing gaseous constituents in an exhaled gas flow, comprising:
means for obtaining a gas sample from said exhaled gas flow wherein said gas sample comprises a mixture of gas and liquid;
fast-response means, connectable to said means for sampling, for obtaining a substantially dry gas sample from said mixture of liquid and gas, comprising:
a microvolume separation chamber defined by a first end surface, a second end surface, and a side wall surface;
inlet port means for introducing said gas sample to said separation chamber in a radial direction towards the center of said separation chamber;
first outlet port means for removing substantially dry gas for said analyzing, positioned in said first end surface;
second outlet port means for removing a waste mixture of gas and liquid from said separation chamber for disposal positioned in said second end surface; and
at least one substantially gas-impermeable body, having a surface, positioned in said separation chamber and movable with respect to said surface;
between a first position and a second position, said first position being closer to said second outlet port means than said second position, said gas-impermeable body, in said first position spaced from said second end surface to produce at least a first capillary volume effective to convey at least some of said liquid toward said second outlet port means, said first capillary volume being at least partially defined by at least a portion of said surface of said gas-impermeable body; and
said microvolume separation chamber and said gas-impermeable body together defining an effective separation volume being the volume of said microvolume separation chamber minus the volume of said gas-impermeable body;
wherein substantially dry gas is provided at said first outlet port means;
means for determining the presence of at least one gaseous constituent in a substantially dry gas; and
means for conveying gas from said second outlet port to said means for determining the presence of at least one gaseous constituent.

41. An apparatus, as claimed in claim 40, wherein:
said means for separating liquid is detachable from said apparatus.

42. An apparatus for separating liquid from a mixture of liquid and gas, comprising:
a separation chamber defined by a first substantially hemispherical end surface having a first radius, a second substantially hemispherical end surface having a second radius greater than said first radius, and a side wall defining a portion of a conical surface extending between said first end surface and said second end surface;
an inlet port formed in said side wall:
a first outlet port formed in said first end surface;
a second outlet port formed in said second end surface;
a plurality of fins extending inward into said separation chamber from said second end surface and said side wall; and
at least one substantially gas-impermeable spherical body positioned in said separation chamber to permit contact between said spherical body and at least a portion of said fins, said spherical body movable from a first position spaced from said first outlet port to a second position substantially occluding said first outlet port;
wherein when said separation chamber is tilted at an angle greater than a predetermined angle, said spherical body is automatically positioned in said second position; and
wherein said spherical body is positionable to form a capillary-sized volume with respect to said liquid in cooperation with at least one of said fins and said side wall.

43. An apparatus, as claimed in claim 42, wherein:
said portions of said fins contactable with said spherical body are substantially flat.

44. In a system for analyzing samples of an exhaled mixture of gas and liquid, a fast-response apparatus usable for obtaining a substantially dry gas sample from a sample of said mixture of gas and liquid, comprising:
a microvolume separation chamber for separating said gas and said liquid;

inlet port means for introducing a sample of said mixture of gas and liquid into said separation chamber;

first outlet port means for removing substantially dry gas for said analyzing;

a reservoir for holding separated liquid, spaced from said separation chamber;

second outlet port means for removing a waste mixture of gas and liquid from said separation chamber for disposal; and absorbent means disposed in said reservoir for absorbing said liquid in said waste mixture, after said gas and said liquid are separated.

45. In a system for analyzing samples of an exhaled mixture of gases and liquids, a method for obtaining a substantially dry gas sample from a sample of said mixture of gases and liquids, comprising:

providing a microvolume separation chamber defined by a first end wall surface, a second end wall surface, and a side wall surface, said separation chamber having inlet port means and first and second outlet port means, and having a solid body, said solid body having a surface and positioned in said separation chamber and movable with respect to said separation chamber surface, said solid body being spaced from said surface of said separation chamber to produce at least a first capillary volume effective to convey at least some of said liquid toward said second outlet port means, said first capillary volume being at least partially defined by at least a portion of said surface of said solid body:

introducing a sample of said mixture of liquid and gas to said separation chamber through said inlet port in a radial direction towards the center of said separation chamber;

providing a pressure at said first outlet port which is less than the pressure at said inlet port;

providing a pressure at said second outlet port which is less than the pressure at said inlet port, wherein a waste mixture of a portion of said input gas and substantially all of said liquid is moved from said separation chamber through said second outlet port for disposal; and withdrawing substantially dry gas from said first outlet port for said analyzing.

* * * * *